US00PP32316P2

(12) United States Plant Patent
Dofferhof et al.

(10) Patent No.: US PP32,316 P2
(45) Date of Patent: Oct. 13, 2020

(54) ***HYDRANGEA* PLANT NAMED 'B2'**

(50) Latin Name: *Hydrangea paniculata*
Varietal Denomination: B2

(71) Applicant: Greenwood Investments B.V., Reeuwijk (NL)

(72) Inventors: Hans Dofferhof, Reeuwijk (NL); Mike Dofferhof, Reeuwijk (NL)

(73) Assignee: GREENWOOD INVESTMENTS B.V., Reeuwijk (NL)

( * ) Notice: Subject to any disclaimer, the term of this patent is extended or adjusted under 35 U.S.C. 154(b) by 0 days.

(21) Appl. No.: 16/602,445

(22) Filed: Oct. 7, 2019

(30) Foreign Application Priority Data

Sep. 19, 2019 (QZ) ..... PBR 2019/2290

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea paniculata* plant named 'B2' that is characterized by its very short plant height and a very compact plant habit with the habit maintained after 2 years when grown in the landscape, its large panicles relative to its plant size held on strong stems, its upright plant habit, and its sterile flowers that are light green-creamy white in color and become slightly flushed with rose pink as they age.

2 Drawing Sheets

Botanical classification: *Hydrangea paniculata.*
Varietal denomination: 'B2'.

CROSS-REFERENCE TO A RELATED APPLICATION

This application claims priority to European Community Plant Variety Office (CPVO) Plant Breeder's Rights Application No. 2019/2290 filed on Sep. 19, 2019 under 35 U.S.C. 119(f), the entire contents of which is incorporated by reference herein.

BACKGROUND OF THE INVENTION

The present invention relates to a new and distinct cultivar of *Hydrangea paniculata* and will be referred to hereafter by its cultivar name, 'B2'. 'B2' represents a new panicle *hydrangea*, a perennial shrub grown for landscape use and as a potted plant.

'B2' was discovered as a chance seedling by the Inventors in Reeuwijk, The Netherlands in August of 2016. The parent plants are unknown.

Asexual propagation of the new cultivar was first accomplished by stem cuttings by one of the Inventors in May of 2017 in Reeuwijk, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'B2' as a unique cultivar of *Hydrangea paniculata.*

1. 'B2' exhibits a very short plant height and a very compact plant habit with the habit maintained after 2 years when grown in the landscape.
2. 'B2' exhibits large panicles relative to its plant size held on strong stems.
3. 'B2' exhibits an upright plant habit.
4. 'B2' exhibits suitability as a potted plant.
5. 'B2' exhibits sterile flowers that are light green-creamy white in color and become slightly flushed with rose pink as they age.

'B2' can be most closely compared to the *Hydrangea paniculata* cultivars 'ILVOBO' (U.S. Plant Pat. No. 22,782) and 'Jane' (U.S. Plant Pat. No. 22,330). Both are similar to 'B2' in being considered to have dwarf plant habits. 'ILVOBO' differs from 'B2' in having sterile flower sepals that are brighter white-light green in color, inflorescences that are more rounded in shape, and a less compact plant habit. 'Jane' differs from 'B2' in having sterile flower sepals that turn darker pink in fall, inflorescences that are more rounded in shape, and a less compact plant habit.

BRIEF DESCRIPTION OF THE DRAWINGS

The accompanying colored photographs illustrate the overall appearance and distinct characteristics of the new *Hydrangea*. The photographs were taken of a two-year-old plant of 'B2' as field grown in Reeuwijk, The Netherlands and placed in a 10-liter bucket for the photographs in Boskoop, The Netherlands.

The photograph in FIG. 1 provides a side view of the plant habit of 'B2' in bloom.

Figure 1:
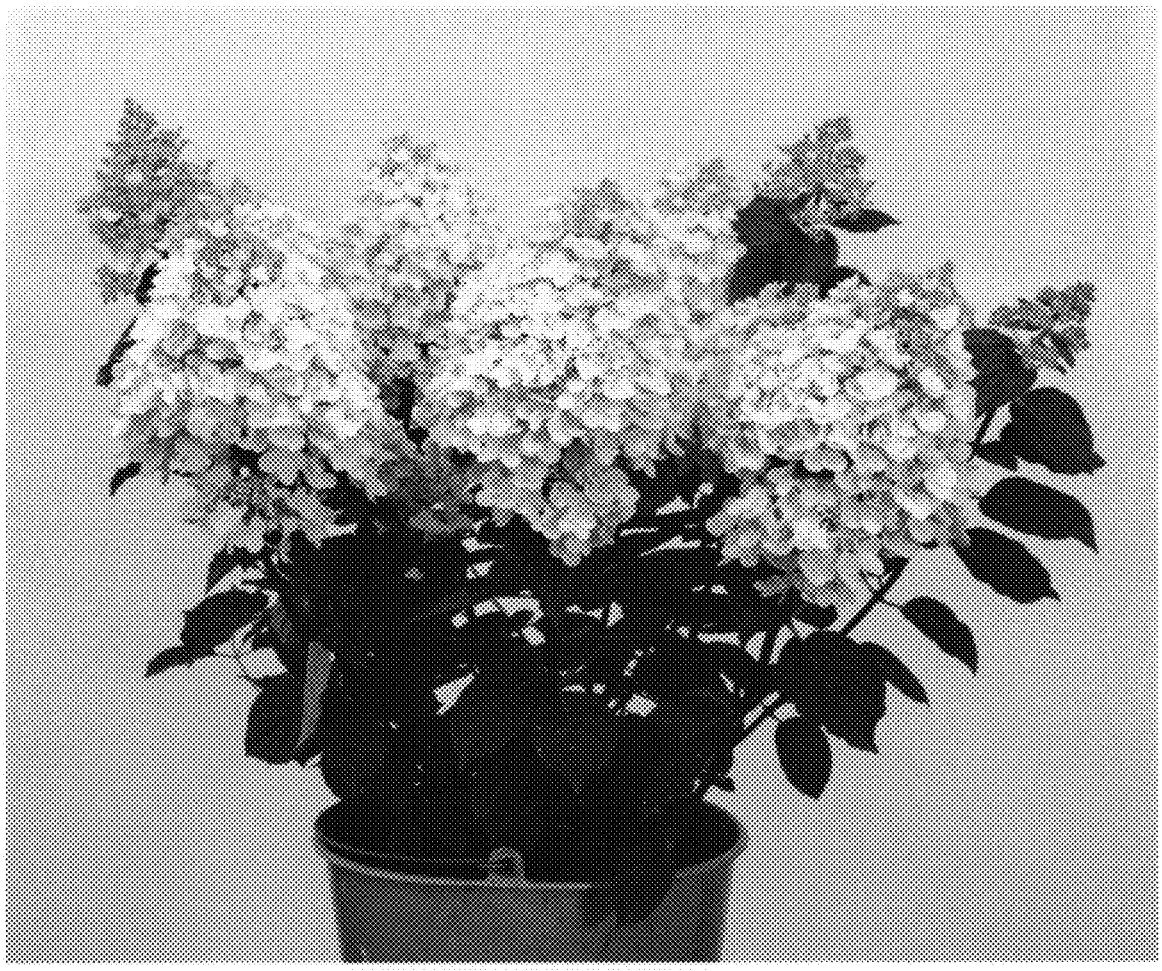
Figure 2:
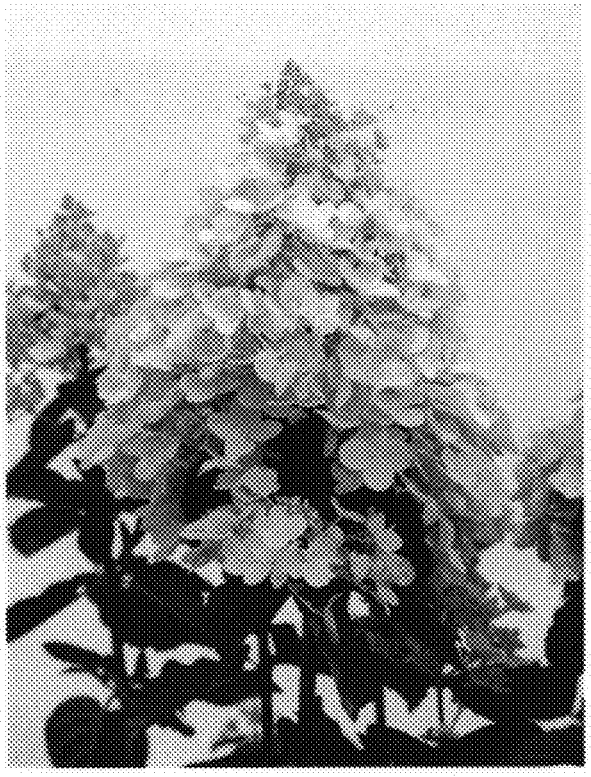

The photograph in FIG. 2 provides a close-up view of an inflorescence of 'B2'.

Figure 3:
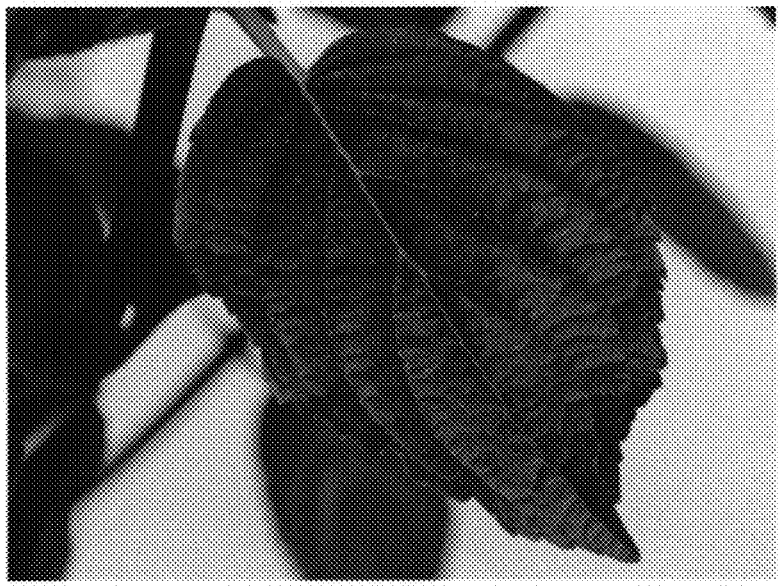

The photograph in FIG. 3 provides a close-up view of a leaf of 'B2'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'B2' as field grown in Reeuwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July and August in the Netherlands.

*Plant type*.—Upright and very compact.

*Height and spread*.—Reaches 55 cm in height and 79.5 cm in spread as a 2-year-old plant in the landscape.

*Hardiness*.—At least in U.S.D.A. Zones 5 to 9.

*Diseases and pests*.—No susceptibility and resistance to diseases or pests has been observed.

*Root description*.—Fine, fibrous and dense, NN155A and 164A in color.

*Propagation*.—Stem cuttings.

*Root development*.—An average of 6 weeks for root initiation with a finished plant produced in about 12 months.

*Growth rate and vigor*.—Moderate.

Stem description:

*Stem shape*.—Rounded.

*Stem strength*.—Strong.

*Stem color*.—Young; 144B, mature; 147D, upper surface (sunny side) 184A, old bark; N199C and 200D.

*Stem size*.—Average of 40.2 cm in length (excluding inflorescence) and 6 mm in diameter.

*Stem surface*.—Young stems are matte and densely covered with stiff hairs, average of 0.5 mm in length and match surface color, mature stems are matte and moderately covered with lenticels that are an average of 1.5 mm in length and 0.75 mm in diameter, 165C in color.

*Stem aspect*.—Upright, average of 55° to soil level.

*Internode length*.—An average of 6.5 cm.

*Branching*.—Freely branching with an average of 16 lateral branches.

Foliage description:

*Leaf shape*.—Broadly ovate.

*Leaf arrangement*.—Opposite.

*Leaf division*.—Simple.

*Leaf base*.—Obtuse to truncate.

*Leaf apex*.—Apiculate.

*Leaf margins*.—Serrate.

*Leaf venation*.—Pinnate, color; upper surface 146B, lower surface 138C.

*Leaf size*.—An average of 8.8 cm in length and 6.4 cm in width.

*Leaf attachment*.—Petiolate.

*Leaf number*.—An average of 16 per lateral stem.

*Leaf surface*.—Both surfaces; matte and slightly rugose, upper surface sparsely covered with short hairs, average of 0.3 mm in length, too small to measure color, lower surface very sparsely covered with very short hairs an average of 0.4 mm in length and too small to measure color.

*Leaf color*.—Young upper surface; 137A, young lower surface 146B, mature upper surface; NN137A to NN137B, mature lower surface; a blend of 147B and 191A.

*Petioles*.—An average of 1.9 cm in length and 1.75 mm in diameter, upper surface color 144B, lower surface color 144B, tinged with 172B, both surfaces matte, upper surface sparsely covered with short hairs, average of 0.3 mm in length, too small to measure color, lower surface very sparsely covered with very short hairs an average of 0.4 mm in length and too small to measure color.

Inflorescence description:

*Inflorescence type*.—Terminal conical panicle, comprised of sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 21.9 cm in height and 17.7 cm in diameter.

*Flower number*.—An average of 350 sterile flowers and 1,600 fertile flowers per panicle.

*Flower fragrance*.—Faint, sweet and pleasant.

*Flower aspect*.—Sterile flowers; held upright to outward and slightly drooping, fertile flowers; held upright from peduncle.

*Flower size*.—Sterile flowers; up to 3.1 cm in diameter and 1 cm in depth, fertile flowers; an average of 6 mm in diameter and 3 mm in depth.

*Flower type*.—Sterile flowers rotate, fertile flowers rotate, dropped when mature.

*Flower buds*.—Sterile flowers; an average of 6 mm in length and 9 mm in diameter, cup-shaped, 145C in color, fertile flowers; an average of 3 mm in length and diameter, obovate in shape, color; 145B to 145C, top 65A, immature calyx 147D.

*Petals*.—Sterile flowers; 4 (occasionally 5), ovate to concave in shape, acute apex, entire margins, cuneate base, up to 2.5 mm in length and 1.5 mm in width, both surfaces; glabrous and matte, color when opening and fully open upper surface 157B, changing to 157D at the margins, color when opening and fully open lower surface 157D, fertile flowers; 4 (occasionally 5), rotate and cruciform in shape, ovate to concave in shape, acute apex, cuneate base, entire margins, average of 2.5 mm in length and 1.5 mm in width, both surfaces glabrous and matte, color; upper surface when opening and fully open 157B, changing to 157D at the margins, lower surface when opening and fully open 157D, petals drop at maturity.

*Peduncles*.—Primary peduncles; strong, flattened oval in shape, an average of 3 cm in length and 2 mm in width. secondary peduncles 2 cm in length and 2 mm in width, 157A in color, surface is matte and moderately covered with thin pubescence an average of 0.4 mm in length and 145D in color.

*Pedicels*.—Sterile flowers; moderate strength, an average of 1.7 cm in length and 1 mm in width, 157A in color, surface is pubescent, held at a 60° angle, 145D in color, surface is matte and moderately covered with thin pubescence an average of 0.4 mm in length and 145D in color, fertile flowers; moderate strength, an average of 1.5 mm in length, 0.5 mm in diameter, held at a 20° angle, 145D in color, surface is matte and densely covered with thin pubescence an average of 0.4 mm in length and 145D in color.

*Sepals*.—Sterile flowers; 4 (occasionally 5), rotate, broad ovate to elliptic and broadly obovate in shape, obtuse to broadly bluntly acute apex, rounded to cuneate base, entire margins, cuneate base, up to 1.8 cm in length and 1.6 cm in width, both surfaces; glabrous and matte, color; upper surface when opening 150D, changing to 150C at the base, lower surface when opening 150D, upper surface when fully open color between 145B and 145C, lower surface when fully open 145C, upper and lower changing to 186D as they age in fall, fertile flowers; 5, rotate, near deltoid in shape, broad acuminate apex, broad cuneate base, entire margins, 1 mm in length, 1.5 mm in width, both surfaces glabrous and matte, upper and lower surface when opening and fully open 144C in color.

*Bracts*.—Sterile flowers; 2 alternately to nearly opposite are present on each pedicel, oblanceolate in shape, narrow acute apex, narrow cuneate base, entire margins, 8 mm in length, 3 mm in width, upper surface color 144D, lower surface color 145C, fertile flowers.

Reproductive organs:

*Gynoecium*.—Sterile flowers; not present, fertile flowers; 3 pistils, an average of 1.25 mm in length, stigma; club-shaped and 155C in color, style; 0.75 mm in length, 157D in color, ovary is 147D in color.

*Androecium*.—Sterile flowers; stamens; average of 8, filaments; 1 mm in length and 157D in color, anthers; broad oblong in shape, 0.5 mm in length, 155A in color, pollen; moderate in quantity, 155D in color, fertile flowers; stamens; average of 8, filaments; 2 mm in length, 157B in color, anthers; broad oblong in shape, 0.5 mm in length, 155A in color, pollen; moderate quantity, 155D in color.

*Fruit and seed*.—None observed to date.

It is claimed:

1. A new and distinct cultivar of *Hydrangea* plant named 'B2' substantially as herein illustrated and described.

* * * * *